United States Patent [19]
Weatherbury et al.

[11] Patent Number: 6,146,903
[45] Date of Patent: Nov. 14, 2000

[54] METHOD FOR DETERMINATION OF WATER TREATMENT POLYMERS

[75] Inventors: Pauline Weatherbury, Manchester; William H. Stemson, Glasgow, both of United Kingdom

[73] Assignee: Strategic Diagnostics Inc., Newark, Del.

[21] Appl. No.: 08/296,272

[22] Filed: Aug. 25, 1994

Related U.S. Application Data

[63] Continuation of application No. 07/951,963, Sep. 28, 1992, abandoned.

[30] Foreign Application Priority Data

Feb. 29, 1992 [GB] United Kingdom ............... 9204409

[51] Int. Cl.$^7$ ..................... G01N 37/53; C12P 21/04; C07K 16/00
[52] U.S. Cl. ................. 436/548; 435/7.92; 435/7.93; 435/7.94; 435/7.95; 435/70.21; 436/547; 436/815; 530/388.1; 530/388.9; 530/389.1; 530/389.8
[58] Field of Search .................. 435/7.92, 7.93, 435/7.94, 7.95, 240.2, 240.28, 70.21; 436/547, 548, 815; 530/388.1, 388.9, 389.1, 389.8

[56] References Cited

U.S. PATENT DOCUMENTS

| | | | |
|---|---|---|---|
| 4,046,707 | 9/1977 | Smith et al. ....................... | 252/180 |
| 4,126,549 | 11/1978 | Jones et al. ....................... | 210/58 |
| 4,704,440 | 11/1987 | Goulding et al. .................. | 525/376 |

FOREIGN PATENT DOCUMENTS

| | | |
|---|---|---|
| 260829 | 3/1988 | European Pat. Off. . |
| 535347 | 4/1993 | European Pat. Off. . |
| 540314 | 5/1993 | European Pat. Off. . |
| 8809798 | 12/1988 | WIPO . |

OTHER PUBLICATIONS

American Type Culture Collection Catalogue of Cell Lines & Hybridmas Fifth Edition, 1985 p 213.

Kohler & Milstein, Nature 256 Aug. 7, 1975 pp 495–497.

Mikulska et al Archium Immunologiae et Therapiae Experimentalis 26 (1978) pp 73–76.

Südi et al. Kieler Milchwirtschaftliche Forschungs berichte 40 (1988) pp 179–203.

*Primary Examiner*—Jyothsan Venkat
*Assistant Examiner*—Joseph W. Rigiliano
*Attorney, Agent, or Firm*—Kilpatrick Stockton LLP

[57] ABSTRACT

A method for determining the presence and/or concentration of a water treatment polymer in an aqueous sample, comprising producing a polyclonal or monoclonal antibody to the water treatment polymer, and using the antibody so produced as a reagent in an immunoassay, conducted on the aqueous sample.

7 Claims, 1 Drawing Sheet

METHOD FOR DETERMINATION OF WATER TREATMENT POLYMERS

This application is a continuation of application Ser. No. 07/951,963, filed Sep. 28, 1992 abandoned.

BACKGROUND OF THE INVENTION

The present invention relates to a determination method, in particular to a method, based on immunoassay, for the determination of water treatment chemicals in aqueous media, and to novel antibodies and hybridomas useful in the new method.

The majority of natural waters, and aqueous systems in general, contain dissolved salts of metals such as calcium, magnesium, barium and strontium. When the natural water or aqueous system is heated, the dissolved salts may be converted to insoluble salts, and thereupon deposited as scale on any heat transfer surfaces in contact with the water or aqueous system. Insoluble salt scale may be formed even when the water or aqueous system is merely concentrated, without being heated.

Such precipitation and scale deposition are troublesome and can result in an increase in the costs required to maintain aqueous systems in good working order. Among the problems caused by scale deposits are obstruction of fluid flow, impedance of heat transfer, wear of metal parts, shortening of equipment life, localised corrosion attack, poor corrosion inhibitor performance and unscheduled equipment shutdown. These problems can arise, e.g. in any circulating water system such as those used in oil drilling wells, steam power plants, water desalination plants, reverse osmosis equipment, heat exchange equipment and equipment concerned with the transport of products and by-products in aqueous media, e.g. fly-ash formed during the combustion of coal, in the production of electricity.

A number of additives, notably polycarboxylates, have been provided as effective scale inhibitors for addition to aqueous systems.

Likewise, natural waters and aqueous systems are corrosive towards metals which are in operational contact with them. Consequently, such aqueous systems must be treated with a corrosion inhibitor, e.g. a phosphonate, in order to prevent deterioration of such metals, e.g. pipelines.

Although water treatment chemicals can be effective at very low concentrations, a certain minimum concentration must be maintained if the aqueous system is to operate trouble-free. With the passage of time, loss of the water treatment chemical from the system occurs and replenishment is necessary to avoid the above-mentioned operational problems. On the other hand, use of excess of water treatment chemical increases operational costs. The need to balance treatment, chemical effectiveness and cost has led, therefore, to the development of methods and devices for monitoring the level of water treatment chemicals in aqueous systems.

For example, colourimetric methods are available for the determination of scale inhibitors, e.g. polycarboxylates. Colorimetric methods, however, have the disadvantage that they are subject to interference from extraneous materials. In oil field applications, for instance, interference arises mainly from iron and oil-derived organic materials.

In an attempt to overcome this interference problem, a sample-preparation (pretreatment) cartridge maybe employed, in which interfering species are removed and the water treatment chemical is concentrated. Unfortunately, however, such techniques can result in loss of the water treatment chemical being determined due to competition from the organics for adsorption sites on the cartridge. Such methods are time consuming, lack robustness and the required sensitivity (limits of detection only 1–2 ppm). In addition they require a certain amount of expertise in order to be used effectively to conduct the required determination.

More recently, immunological methods have been developed for the determination of organic compounds.

Immunological methods for determining proteins, cells, hormones, vitamins, drugs and mycotoxins etc. have been known for many years, and have been widely reported in the literature. In such methods, an animal, often a mouse or rabbit, is immunized, either with an analyte or a protein-analyte conjugate. The antibodies produced by the animal are then used, in the form of an immunoassay, to determine the analyte. These methods are based upon the specific reaction between the analyte and the antibody.

The immunoassays which have been reported in the literature incorporate antibodies that have been raised to natural molecules. Recently, however, EP 260829A, has disclosed novel mono- and polyclonal antibodies which are reactive with chlorinated phenols, especially pentachlorophenol. The antibodies can then be used to identify and assay pentachlorophenol, which is widely used as a pesticide and preservative.

We have now succeeded in applying an immunoassay method to the detection of water treatment polymers in aqueous solution, to provide a determination method which is sensitive, specific, rapid, robust and which can be operated by relatively inexperienced personnel—this has not been achieved by such methodology before the present application.

SUMMARY OF THE INVENTION

It is surprising that an antibody can be raised effectively to molecules which are polydisperse i.e. having differing molecular weights which vary considerably in size and shape. The competitive assay results demonstrate that the antibodies are raised to the core active centre of the molecules i.e. a moiety which is present in every molecule in the product although the number of repeating monomer units can vary.

Accordingly, the present invention provides a method for determining the presence and/or concentration of a water treatment polymer in an aqueous sample, comprising the production of polyclonal or monoclonal antibody to the water treatment polymer, and using the antibody so produced as a reagent in an immunoassay conducted on the aqueous sample.

The present invention also provides a method for determining the presence and/or concentration of a water treatment polymer in an aqueous sample, comprising an effective amount of a monoclonal antibody or polyclonal antibody which has been raised to the water treatment polymer, in association with an acceptable carrier.

DETAILED DESCRIBTION

Figure 1:
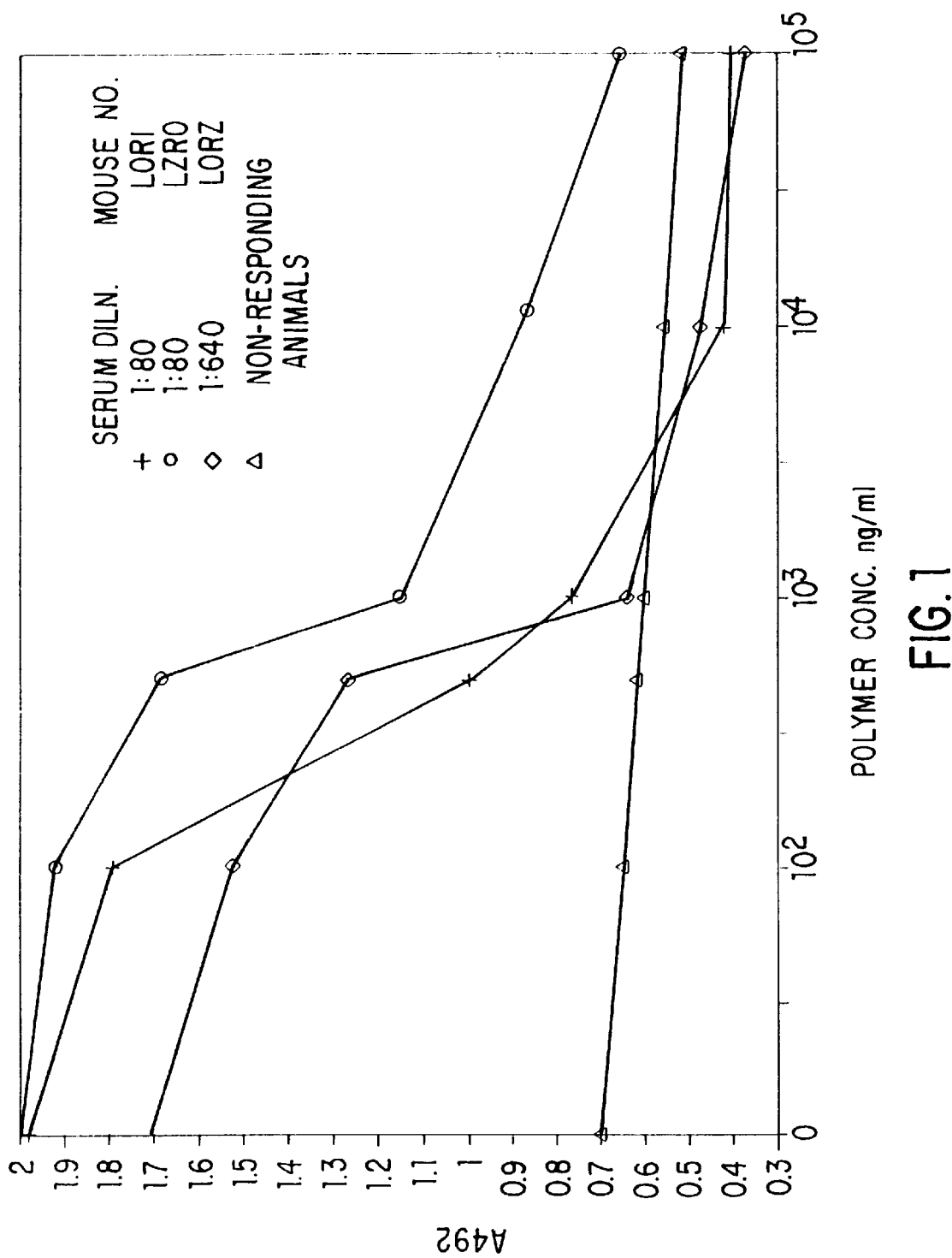
FIG. 1 is a plot comparing the sensitivity (absorbance versus polymer concentration) of EUSA (Enzyme Linked Immunogenic Sorbent Assay) procedures based on polyclonal or monoclonal antibodies in the conjugated form and the same antibodies in the free form, as described under "EUSA Procedures" in Example 1.

Preferred water treatment polymers, for determination in the process of the present invention, are phosphorus acid containing carboxylic acid telomers having the formula I:

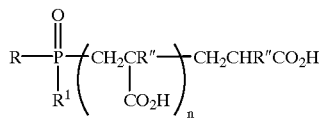

I or salts thereof, in which R" is hydrogen, methyl or ethyl, R is hydrogen, $C^1-C_8$ alkyl, $C_5-C_{12}$ cycloalkyl, aryl, aralkyl, a residue of formula:

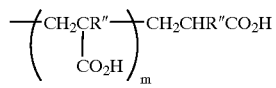

in which R" has its previous significance and the sum of m and n is an integer of at most 100, or R is a residue—OX in which X is hydrogen or $C_1-C_4$ alkyl, and $R^1$ is a residue—OX in which X has its previous significance.

The telomers of formula I, and their production are described in more detail in U.S. Pat. No. 4,046,707.

Particularly preferred telomers of formula I are those having the formula IA:

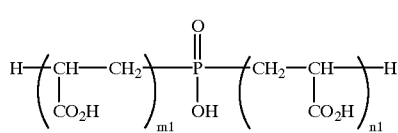

IA in which the sum of m' and n' is an integer ranging from 4 to 32, especially, 15 to 20.

Other preferred water treatment polymers, for determination in the process of the present invention are hydrolyzed terpolymers of maleic anhydride with other monomers the molar ratio of maleic anhydride to the other monomers ranging from 2.5:1 to 100:1 and the molecular weight of the terpolymer being below 1000. Such terpolymers are described in U.S. Pat. No. 4126549.

Preferred ratios of monomers in the terpolymer are in the range of 2½–3½:1 of maleic anhydride to other monomers. Preferred other monomers are vinyl acetate acid and ethyl acrylate.

These ratios are those used in the preparation of the cotelomer of formula II and are not necessarily the ratios to be found in the final cotelomer.

Other examples of preferred water treatment molecules include other polyacrylic acid polymers; copolymers of acrylic acid and acrylamidomethylpropane sulphonic acid (AMPS); copolymers of acrylic acid and vinyl acetate; polymaleic acid; hydrolysed polymaleic acid; terpolymers of maleic acid, ethyl acrylate and vinyl acetate; copolymers of acrylic acid and maleic anhydride; copolymers of maleic acid and sodium allyl sulphonate; and copolymers of maleic anhydride and sulphonated styrene-and vinyl sulphonic acid telomers.

With respect to aqueous systems in which water treatment polymers to be determined may be present, of particular interest are the aqueous systems employed in plant cooling water steam generating plants, sea-water evaporators, reverse osmosis equipment, paper manufacturing equipment, sugar evaporator equipment, soil irrigation plant, hydrostatic cookers, gas scrubbing systems, closed circuit heating systems, aqueous-based refrigeration systems and down-well systems.

The antibody used in the method and composition of the present invention may be produced by known techniques.

For the production of polyclonal antibodies which are reactive with a particular water treatment polymer, firstly an immunogenic conjugate of the polymer and a macromolecule carrier may be produced; an animal may then be immunized with the conjugate, the polymer alone, adjuvant or a discrete mixture of each; blood may be removed from the animal and the serum separated from the blood; and finally the polyclonal antibodies may be recovered from the serum.

It may be preferred, however, to use monoclonal antibodies, which are reactive with specific epitopes on the water treatment polymer, in the method and composition of the present invention, especially in view of their superior specificity for a particular polymer. Monoclonal antibodies may be obtained by the technique first described by Kohler and Milstein, Nature, 265:495 (1975). This technique comprises providing an immunogenic form of the specific water treatment polymer, immunizing an animal with such; obtaining antibody-producing cells from the animal; fusing the cells so obtained with myeloma cells to produce hybridomas; selecting from the hybridomas a hybridoma which produces an antibody which reacts with the specific water treatment polymer, and then isolating the monoclonal antibody from the selected hybridoma Water treatment polymers generally have low molecular weights and do not, per se, induce the production of antibodies. They can be used as a hapten, however, in combination with a higher molecular weight, immunogenic carrier, such as a protein, using e.g. the technique disclosed by Albro et al. Toxicol Appl. Pharmacol 50, 137–146 (1979).

The conjugate so obtained may then be used to immunize an animal host, by conventional techniques, e.g. inoculation. The animal host may be, e.g. a rabbit or a rodent such as a rat or mouse.

After the host animal has produced antibodies to the administered conjugate, polyclonal antibodies may be recovered from the animal by conventional techniques.

For example, blood may be removed from the animal and serum may be separated from the blood so removed. The desired antibodies may then be removed from the serum, e.g. by affinity purification or salt fractionation.

To produce monoclonal antibodies to the water treatment polymer, cells which produce antibodies may be recovered from the immunized animal. B lymphocytes removed from the animal's spleen are preferred.

The removed cells are fused with myeloma cells to produce hybridomas, which are then separated, again using standard techniques such as cloning by limiting dilution.

Once the hybridomas have been separated a selection is made to ascertain those which produce antibodies to the specific water treatment polymer to be determined in the method of the present invention. The relevant specific hybridomas can then be isolated by known methods, and the relevant antibodies secreted from them by conventional techniques.

The following examples further illustrate the present invention.

EXAMPLE 1

1. Preparation of Protein Conjugates

A telomer (Telomer 1) derived from 16 moles of acrylic acid and 1 mole of hypophosphorous acid and produced by the method of U.S. Pat No. 4,046,707 is bound to a carrier protein keyhole limpet haemocyanin (KLH) using 1-ethyl-3-(3-dimethylaminopropyl)-carbodiimide hydrochloride (EDC). In addition the product is bound to a second protein, ovalbumin (OVA) for screening purposes.

Essentially 2mg of KLH or OVA are dissolved with 200 µl of deionized water. In addition, 2 mg of the peptide to be coupled are dissolved in 0.5 ml of conjugation buffer (0.1M (2-(N-morpholino)-ethanesulfonic acid) MES, 0.9 M sodium chloride NaCl and 0.02% sodium azide $NaN_3$, pH 4.7).

The 500 µl of peptide solution are added to the 200 µl of carrier protein solution. For OVA conjugation, this solution is added to 10 mg of EDC and dissolved by gentle mixing. For KLH conjugation, the 10 mg of EDC are dissolved in 1ml of deionized water and 501 µl of this solution are added immediately to the carrier—peptide solution.

The reaction proceeds for 2 hours at room temperature. Any precipitate is removed using centrifugation prior to purification.

The conjugate is purified using gel filtration or Sephadex G50 (0.5×5 cm). The column is washed using 5 ml of phosphate buffered saline (PBS). The peptide carrier mixture is applied directly to the top of the column and the eluate collected. 0.5 ml aliquots of PBS are added and each fraction is collected in a separate tube. 15 mls of PBS are added to elute both the conjugate and the peptide. The immunogen elutes between fractions 4–6, and the free peptide and reagents after fraction 8.

The hapten—carrier ratios are determined spectrophotometically and by assessment of the concentrations of the reactants following conjugation. The molar ratio of polymer per 100,000 mol. wt of carrier is 6–11.

2. Immunisation of Animals a) Mice (NZB/NZW Fl hybrid females and BALB-c females), 6–8 weeks old, receive 0.2 mg polymer in 0.1 ml 0.15 M NaCl solution (saline) mixed with 0.1 ml Freunds complete adjuvant (FCA) and 100 µg polymer conjugate (by protein concentration) in 0.1 ml saline. Thereafter animals are injected every 18–21 days with the same antigen preparations and doses except that Freunds incomplete adjuvant (FIA) is substituted for FCA. All injections are intraperitoneal and animals sacrificed for blood or spleens.

b) Rats (Sprague-Dawley females) aged 12–16 weeks are injected with the identical protocol indicated in (2a). Blood is obtained by heart puncture.

c) Rabbits (NZW—female) aged 4 months, are injected as follows—day 0, intramuscular; day 14, intramuscular, day 24 intraperitoneal. All treatments contain 50 ug protein or 200 ug polymer/0.2 ml and are given in conjunction with 0.2 ml FCA (day 0), 0.2 ml FIA (day 14), 0.2 ml saline (day 24). Blood is obtained on day 34 by venepuncture, allowed to clot at room temperature and the serum separated by centrifugation (2000g, 15 min, 4° C.).

3. Monclonal Antibody Production

Mice, immunised as indicated above, are injected with polymer or conjugate (at the doses shown in 2a) 3 days prior to sacrifice.

The spleens are removed and the splenocytes isolated by dissection into Hanks Balanced Salt Solution. These spleen cells are fused with cells from the X63.Ag 8 6.5.3 murine myeloma line, in exponential growth, in a ratio of 4:1 by the addition of lml 46% (w/v) polyethylene glycol 1550 (Serva) in RPMI 1640 with gentle mixing for 3 min at 37° C. After standing for 2 min at room temperature, the mixture is slowly diluted by the drop-wise addition of 20 ml RPMI 1640 over 5 min, followed by standing at room temperature for 10 min. After washing twice with RPMI 1640, the cells are incubated for 2 hr at 37° C. in bicarbonate-buffered RPMI 1640, supplemented with 10% (v/v) fetal calf serum, 2 mmol/l L-glutamine, 50 Iu/ml penicillin and 50ug/ml streptomycin (Flow) and containing $1 \times 10^{-4}$ mol/l hypoxanthine and $1.6 \times 10^{-31\ 5}$ mol/l thymidine (HT medium). The cell suspensions (100 ul) are then dispensed into 96-well tissue culture plates (Costar) at three different concentrations (2.5, 1.25 and $6 \times 10^{-6}$ cells/ml). Finally, 200 g ul HT medium containing $4 \times 10^{-7}$ mol/l aminopterin (HAT medium) are added to each well. The plates are incubated at 37° C. in a humidified atmosphere of 5% $CO_2$ in air. Hybridoma cells are initially grown in HAT medium but this is eliminated after 14 days by step-wise replacement with HT medium. Supernatant liquids are screened for specific antibody by indirect non-competitive ELISA 14–18 d post-fusion. Specific hybridomas are subsequently expanded into flasks and cloned three times or until 100% cloning efficiency is obtained. This procedure is carried out by limiting dilutions in 96-well tissue culture plates containing a feeder layer of spleen cells ($2 \times 10^5$ cells/well) from non-immunized NZB/DALB-C hybrid mice. Cell lines of interest are maintained in vitro in culture medium and are frozen, at a concentration of $5 \times 10^6$ cells/ml, in RPMI 1640 containing 30% bovine serum and 15% dimethyl sulphoxide (Sigma) and stored in liquid nitrogen (Islam, M. S. and Stimson, W. H. Lett. Appld. Microbiol., 4, 85–89 (1987).

4. ELISA Procedures a) Indirect non-competitive ELISA—for screening hybridoma supernatants and sera from animals for the presence of antipolymer antibodies.

i) Flat-bottomed 96well microtire plates (Dynatech) are coated with polymer conjugate—10 ug protein/lml 0.02M Tris/HCl buffer, pH 9.0. Aliquots (100 ul per well) are distributed into microtitre plates and incubated for 1 h at 37° C. The solution is then removed and replaced with 100 ul 1% (w/v) BSA solution in 0.02M Tris/HCl, pH 9.0, for 30 min at 37° C. Thereafter, the plates are washed (×4) with 0.2M Tris/HCl buffer pH 7.4 containing 0.2M NaCl and 0.05% (v/v) Tween 20 (wash buffer). These plates may be dried in vaccuo and stored dry for up to one year or used immediately for assays.

ii) Hybridoma supernatants or animal sera (dilutions 1:10 to $1:10^5$ commonly) are added to the plates—100 ul per well. Following incubation for 45 min, 37° C. the plates are washed ×3 with wash buffer.

iii) Sheep anti-mouse γ-globulins—horse radish peroxidase conjugate (SAPU, Carluke, Scotland) is diluted 1:2000 in 0.15M NaCl containing 25% (v/v) sheep serum. Aliquots (100 ul) are added to each well and incubated for 45 min at 37° C. before washing ×3 with wash buffer. Enzymic activity (A450) is measured with 200 ul tetramethylbenzidine substrate, pH 5.5, the reaction is stopped after 30 min, room temperature with 50 ul 2M $H_2SO_4$.

b) Sandwich ELISA—for estimating polymer concentrations in samples.

i) Antisera are precipitated with $(NH4)_2SO_4$ solution and redissolved in 0.15M NaCl solution to give a concentration of 15 mg/ml. This is diluted in 0.02M Tris/HCI, pH 9.0 from 1:500 to 10,000 and used to coat microtitre plate wells (100 ul per well) for lh at 37° C. The plate is washed ×5 with wash buffer before use.

ii) Polymer standards (10 ng/ml to 20ug/ml) 0.15M NaCl solution and samples (100 ul) are added to wells for 45 min at 37° C. The plate is washed ×3 in each buffer.

iii) Antibody/antiserum—enzyme conjugate preparation is achieved by periodate coupling of horse radish peroxidase (HRP).

5 mg of HRP is resuspended in 1.2 ml of water. 0.3 ml of freshly prepared 0.1M sodium periodate in 10mM sodium phosphate (pH 7.0) is added.

The solution is incubated at room temperature for 20 min prior to dialysing the HRP solution versus 1mM sodium acetate (pH 4.0) at 4° C. with several changes overnight.

An antibody solution of 10 mg/ml in 20mM carbonate (pH 9.5) is prepared.

The HRP is removed from the dialysis tubing and added to 0.5 ml of the antibody solution and is incubated at room temperature for 2 hr.

The Schiff's bases, thus formed, are reduced by adding 100 ul of sodium borohydride (4 mg/ml in water) and incubated at 4° C. for 2 hr.

The solution is dialyzed versus several changes of PBS.

iv) Antibody-enzyme conjugate (100 ul) prepared as in (iii) and diluted 1:500 to 1:300,00 is added and reaction/readings taken as in [4a(iii)].

c) Competition ELISA i) As for [4a(i)].

ii) Compounds/samples (100 ul) are added to wells and simultaneously 100 ul antibody-enzyme conjugate is added [see 4b (iii +iv)]. The plate is incubated for 45 min at 37° C. and the procedure described in [4a (iii)] carried out.

The results of this procedure are shown in FIG. 1.

RESULTS

Competition assays are performed to detect the free product in a real aqueous sample. OVA conjugate is bound to the walls of microtitration wells and incubated with 1) Polyclonal antiserum raised to the free form (dilution 1:100 to 1:8000) and free product; range 10 ng/ml to 100 µg/ml (c.f. FIG. 1).

2) Polyclonal antiserum raised to the KLH conjugate (dilution 1:100 to 1:35,000) and free product range 10 ng/ml to 100 µg/ml.

3) Monoclonal antibodies raised to the free form (dilution 1:104 to 1:106) and free product range 10 ng/ml to 100 µg/ml and 4) Monoclonal antibodies raised to the KLH conjugate (dilution 1:104 to 1:106) and free product range 10 ng/ml to 100 µg/ml.

Assays incorporating polyclonal or monoclonal antibodies to the conjugated form are sensitive only down to 10 µg/ml. Those incorporating polyclonal and monoclonal antibodies to the free form are sensitive down to 0.1 µg/ml (c.f. FIG. 1).

MATRIX INTERFERENCE

The product is prepared in a variety of synthetic waters and two examples of typical north sea formation water in which the product is commonly applied, to determine matrix interference (see Table 1).

Absorbance (A450) of the positive polymer control in the presence of distilled water is 1.68±0.19 AU. A450 of the negative polymer control is 0.08±0.04 AU. A450 in the presence of the synthetic waters and one of the north sea formation waters was >1.58±0.28 AU. The second formation water brought about a colour change when added to the tetramethylbenzidine substrate.

TABLE 1

| TYPE | COMPOSITION |
|---|---|
| FORMATION 1 | Barium ($Ba^{2+}$) 1050 ppm<br>Calcium ($Ca^{2+}$) 1060 ppm<br>Magnesium ($Mg^{2+}$) 113 ppm<br>Sodium ($Na^+$) 27,986 ppm<br>Chloride ($Cl^-$) 43,196 ppm<br>Potassium ($K^+$) 3833 ppm<br>Strontium ($Sr^{2+}$) 110 ppm |
| SEAWATER 1 | Sulphate ($SO_4^{2-}$) 2426 ppm<br>Sodium ($Na^{2-}$) 22,135 ppm<br>Chloride ($Cl^-$) 34,165 ppm<br>Potassium ($K^+$) 775 ppm<br>Bicarbonate ($HCO_3^-$) 497 ppm<br>THESE ARE MIXED 50/50 or 40/60 OF FORMATION 1/SEAWATER 1 and pH adjusted to 4.5 |
| FORMATION 2 | Barium ($Ba^{2+}$) 252 ppm<br>Calcium ($Ca^{2+}$) 3523 ppm<br>Magnesium ($Mg^{2+}$) 1813 ppm<br>Sodium ($Na^+$) 17,692 ppm<br>Chloride ($Cl^-$) 39,599 ppm<br>Strontium ($Sr^{2+}$) 669 ppm |
| SEAWATER 2 | Sulphate ($SO_4^{2+}$) 2426 ppm<br>Sodium ($Na^{2-}$) 22,135 ppm<br>Chloride ($Cl^-$) 34,165 ppm<br>Potassium ($K^+$) 775 ppm<br>Bicarbonate ($HCO_3^-$) 497 ppm<br>THESE ARE MIXED 50/50 OF FORMATION 2/SEAWATER 2. |
| FORMATION 3 | Calcium ($Ca^{2+}$) 467 ppm<br>Magnesium ($Mg^{2+}$) 75 ppm<br>Potassium ($K^+$) 377 ppm<br>Strontium ($SR^{2+}$) 67 ppm<br>Barium ($Ba^{2+}$) 65 ppm<br>Sodium ($Na^+$) 12,932 ppm<br>Chloride ($Cl^-$) 20,853 ppm |
| SEAWATER 3 | Bicarbonate ($HCO_3^-$) 4000 ppm<br>Sodium ($Na^+$) 1,511 ppm<br>THESE ARE MIXED 75,25 OF FORMATION 3/SEAWATER 3 |
| SOLUTION 4 | Calcium ($Cl^{2+}$) 150 ppm<br>Magnesium ($Mg^{2+}$) 44 ppm<br>Chloride ($Cl^-$) 199 ppm<br>Sodium ($Na^+$) 121 ppm<br>Carbonate ($CO_3^{2-}$) 51 ppm<br>Bicarbonate ($HCO_3^-$) 269 ppm |
| SOLUTION 5 | Calcium ($Ca^{2+}$) 300 ppm<br>Magnesium ($Mg^{2+}$) 88 ppm<br>Chloride ($Cl^-$) 398 ppm<br>Sodium ($Na^=$) 242 ppm<br>Carbonate ($CO_3^{2+}$) 102 ppm<br>Bicarbonate ($HCO_3^-$) 538 ppm |
| SOLUTION 6 | Calcium ($Ca^{2+}$) 20 ppm<br>Magnesium ($Mg^{2+}$) 6 ppm<br>Chloride ($Cl^-$) 30 ppm<br>Sulphate ($SO_4^-$) 21 ppm<br>Bicarbonate ($HCO_3^-$) 18 ppm<br>Sodium ($Na^-$) 46 ppm |
| SOLUTION 7 | Calcium ($Ca^{2+}$) 60 ppm<br>Magnesium ($Mg^{2+}$) 18 ppm<br>Chloride ($Cl^-$) 200 ppm<br>Sulphate ($SO_4$) 200 ppm<br>Bicarbonate ($HCO_3^-$) 427 ppm<br>Sodium ($Na^+$) 83 ppm |
| SOLUTION 8 | Calcium ($Ca^{2+}$) 400 ppm<br>Magnesium ($Mg^{2+}$) 1202 ppm<br>Chloride ($Cl^-$) 18711 ppm<br>Sodium ($Na^+$) 10522 ppm<br>Carbonate ($CO_3^{2-}$) 184 ppm<br>Sulfate ($SO_4^{2-}$) 2623 ppm<br>Potassium ($K^+$) 395 |
| SOLUTION 9 | Caicium ($Ca^{2+}$) 172 ppm<br>Sodium ($Na^+$) 304 ppm<br>Carbonate ($CO_3^{2+}$) 153 ppm<br>Bicarbonate ($HCO_3^-$) 129 ppm<br>Chloride ($Cl^-$) 400 ppm<br>Sulphate ($SO_4^{2-}$) 159 ppm |
| SOLUTION 10 | Calcium ($Ca^{2+}$) 100 ppm |

TABLE 1-continued

| TYPE | COMPOSITION |
|---|---|
| | Magnesium ($Mg^{2+}$) 20 ppm |
| | Chloride ($Cl^-$) 118 ppm |
| | Sodium ($Na^+$) 50046 |
| | Hydroxide ($OH^-$) 36167 |
| | Carbonate ($CO_3^{2-}$) 10556 |
| | Potassium ($K^+$) 2422 |
| SOLUTION 11 | Calcium ($Ca^{2+}$) 23 ppm |
| | Magnesium ($Mg^{2+}$) 10 ppm |
| | Silica ($SiO_2$) 28 ppm |
| | Carbonate ($CO_3^{2+}$) 226 ppm |
| | Phosphate ($PO_4^{2-}$) 74 ppm |
| | Iron ($Fe^{3+}$) 34 ppm |
| SOLUTION 12 | Typical natural sea water sample |
| SOLUTION 13 | Typical north sea formation water Example 1 |
| SOLUTION 14 | Typical north sea formation water Example 2 |

EXAMPLES 2 TO 26

The following compounds of similar structure are substituted in the competion assay, in place of the free product, in the procedure described in Example 1. The results as shown in Table 2 are expressed as a percentage ratio of the mass of polymer giving 50% maximum absorbance to mass of compound of similar structure. The antibody is specific for the determination of phosphinocarboxylic acids.

TABLE 2

| EXAMPLE | COMPOUND | PERCENT CROSS REACTIVITY WITH TELOMER 1 |
|---|---|---|
| 2 | ACRYLIC/ACRYLAMIDE METHYL PROPANO-SULPHONIC ACID (AMPS) COPOLYMER 1 | 2.6 |
| 3 | PHOSPHINIC CARBOXYLIC ACID PCA | 105 |
| 4 | PHOSPHONO CARBOXYLIC ACID | 12.3 |
| 5 | ACRYLIC/AMPS COPOLYMER 2 | 9.7 |
| 6 | POLYACRYLIC ACID 1 | 5.4 |
| 7 | POLYACRYLIC ACID 2 | 8.8 |
| 8 | POLYACRYLIC ACID 3 | 10.5 |
| 9 | ACRYLIC COPOLYMER | 22.7 |
| 10 | POLYACRYLIC ACID 4 | 14.4 |
| 11 | ACRYLIC/AMPS COPOLYMER 3 | 12.7 |
| 12 | ACRYLIC/AMPS/POLY-ETHYLENEGLYCOL COPOLYMER | 9.6 |
| 13 | POLYACRYLIC ACID 5 | 6.6 |
| 14 | 1-HYDROXY ETHYLIDENE-1-1-DIPHOSPHINIC ACID (HEDP)/AMPS COPOLYMER/POLYACRYLIC ACID | 11.4 |
| 15 | PHOSPHONO BUTANE TRICARBOXYLIC ACID (PBTC) | 8.8 |
| 16 | HEDP | 2.1 |
| 17 | PHOSPHONATE 1 | 2.6 |
| 18 | PCA 2 | 91.5 |
| 19 | POLYACRYLIC ACID 6 | 3.0 |
| 20 | PHOSPHONATE 2 | 8.4 |
| 21 | PHOSPHONATE 3 | 9.7 |
| 22 | AMINE OXIDE OF AMINE PHOSPHONATE 1 | 15.6 |
| 23 | AMINE OXIDE OF AMINE PHOSPHONATE 2 | 11.0 |
| 24 | HYDROXYPHOSPHINOUS CARBOXYLIC ACID | 28.2 |

TABLE 2-continued

| EXAMPLE | COMPOUND | PERCENT CROSS REACTIVITY WITH TELOMER 1 |
|---|---|---|
| 25 | ACRYLIC/AMPS COPOLYMER 4 | 11.5 |
| 26 | ACRYLIC/AMPS COPOLYMER 5 | 7.7 |

EXAMPLE 27

Attempts to conjugate the telomer derived from 3 moles of maleic acid 1 mole of vinyl acetate and 1 mole of ethylacrylate with KLH resulted in total precipitation at all reasonable ratios of reactants, as described in Example 1. Low ratio coupling of the product to OVA with EDC is successful (1:4, by weight). In addition low ratio coupling to a second protein, bovine serum albumin (BSA) for screening purposes is also prepared.

Mice and rabbits are immunised as described in Example 1. Antibody production is determined after immobilisation of the second BSA-conjugate onto the walls of a microtitration well and the procedure described in Example 1 is performed.

The conjugated form of the product is shown to be immunogenic. No response is detected from the free form. This is consistent with the size of the molecule being too small ($m_W < 1000$ daltons) to stimulate the immune system.

What is claimed is:

1. A hybridoma which produces antibodies which bind to a polydisperse water treatment polymer, which antibodies can specifically bind with the polymer, the polymer being a phosphinocarboxylic acid of the formula I:

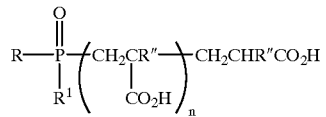

or a salt thereof in which R" is hydrogen, methyl or ethyl; R is hydrogen, $C_1$–$C_{18}$ alkyl, $C_5$–$C_{12}$ cycloalkyl, aryl, aralkyl, a residue of the formula:

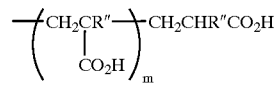

in which R" has is previous significance and the sum of m and n is an integer of at most 100, or a residue —OX in which X is hydrogen or $Cl$-$C_4$ alkyl; and R' is a residue —OX in which X has its previous significance.

2. A cell line comprising a hybridoma according to claim 1 in admixture with a culture medium.

3. A composition useful for determining the presence and/or concentration of a polydisperse water treatment polymer in an aqueous sample, comprising a monoclonal or polyclonal antibody which binds to the water treatment polymer in an immunogenically acceptable carrier; wherein the polymer is a phosphinocarboxylic acid of the formula I:

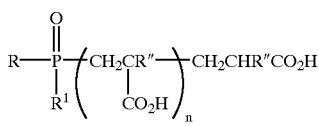

or a salt thereof in which R" is hydrogen, methyl or ethyl; R is hydrogen, $C_1$–$C_{18}$ alkyl, $C_5$–$C_{12}$ cycloalkyl, aryl, aralkyl, a residue of the formula:

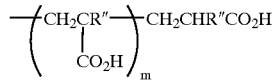

in which R" has is previous significance and the sum of m and n is an integer of at most 100, or a residue —OX in which X is hydrogen or $C_1$–$C_4$ alkyl and R' is a residue —X in which X has its previous significance.

4. An immunoassay method for determining the presence and/or concentration of a polydisperse water treatment polymer in an aqueous sample, comprising (a) contacting a polyclonal or monoclonal antibody which binds to the water treatment polymer with the aqueous sample; (b) incubating the sample with the antibody for a time effective for the antibody to bind to the water treatment polymer to form a complex; and (c) detecting the complex and thereby determining the presence and/or concentration of the water treatment polymer in the aqueous sample; wherein the water treatment polymer is a phosphinocarboxylic acid of the formula I:

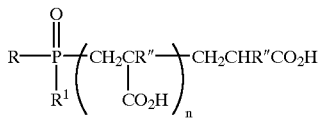

or a salt thereof in which R" is hydrogen, methyl or ethyl; R is hydrogen, $C_1$–$C_{18}$ alkyl, $C_5$–$C_{12}$ cycloalkyl, aryl, aralkyl, a residue of the formula:

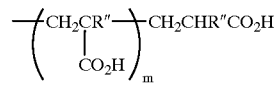

in which R" has is previous significance and the sum of m and n is an integer of at most 100, or a residue —OX in which X is hydrogen or $C_1$–$C_4$ alkyl; and R' is a residue —OX in which X has its previous significance.

5. A method according to claim 4 in which the water treatment polymer has the formula IA:

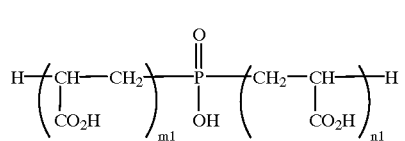

IA in which the sum of m' and n' is an integer ranging from 8 to 32.

6. A method according to claim 5 in which the sum of m' and n' is 16.

7. A method according to any one of claims 4, 5 or 6 in which the aqueous sample is selected from the group consisting or that employed in plant cooling water, steam generating plants, sea-water evaporators, reverse osmosis equipment, paper manufacturing equipment, sugar evaporator equipment, soil irrigation plants, hydrostatic cookers, gas scrubbing systems, closed circuit heating systems, aqueous-based refrigeration systems and down-well systems.

* * * * *

UNITED STATES PATENT AND TRADEMARK OFFICE
CERTIFICATE OF CORRECTION

PATENT NO.    : 6,146,903  
DATED         : November 14, 2000  
INVENTOR(S)   : Pauline Weatherby and William H. Stimson It is certified that error appears in the above-identified patent and that said Letters Patent is hereby corrected as shown below:

Title page,
Both inventors' names have been misspelled on the above-identified patent attached.
The inventors' names should appear as follows,
PAULINE WEATHERBY, MANCHESTER,
WILLIAM H. STIMSON, GLASGOW,
BOTH OF UNITED KINGDOM Signed and Sealed this Fifth Day of February, 2002

Attest:

JAMES E. ROGAN
*Attesting Officer*    *Director of the United States Patent and Trademark Office*